United States Patent
Vavadi et al.

(10) Patent No.: US 10,966,643 B1
(45) Date of Patent: Apr. 6, 2021

(54) WEARABLE NON-INVASIVE CARBON MONOXIDE INHALATION TRACKING

(71) Applicant: Fitbit, Inc., San Francisco, CA (US)

(72) Inventors: Hamed Vavadi, Fremont, CA (US); Lindsey Michelle Sunden, San Francisco, CA (US); Peter W. Richards, San Francisco, CA (US); Chris Hanrahan Sarantos, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 16/439,433

(22) Filed: Jun. 12, 2019

(51) Int. Cl.
*A61B 5/1455* (2006.01)
*A61B 5/00* (2006.01)

(52) U.S. Cl.
CPC ........ *A61B 5/14552* (2013.01); *A61B 5/0002* (2013.01); *A61B 5/6826* (2013.01); *A61B 5/6833* (2013.01); *A61B 2560/0242* (2013.01)

(58) Field of Classification Search
CPC ... A61B 5/0059; A61B 5/0205; A61B 5/1455; A61B 5/14551; A61B 5/14552; A61B 5/6826; A61B 5/6833; A61B 5/0002
See application file for complete search history.

(56) References Cited

U.S. PATENT DOCUMENTS

| | | | | | |
|---|---|---|---|---|---|
| 5,069,214 | A | * | 12/1991 | Samaras | A61B 5/14551 600/323 |
| 5,431,170 | A | * | 7/1995 | Mathews | A61B 5/0002 600/323 |
| 5,964,701 | A | * | 10/1999 | Asada | A61B 5/02438 600/300 |
| 6,397,093 | B1 | * | 5/2002 | Aldrich | A61B 5/14551 600/323 |
| 8,554,297 | B2 | * | 10/2013 | Moon | A61B 5/746 600/323 |
| 2001/0044700 | A1 | * | 11/2001 | Kobayashi | A61B 5/0059 702/31 |
| 2007/0100219 | A1 | * | 5/2007 | Sweitzer | A61B 5/0002 600/323 |
| 2007/0276270 | A1 | * | 11/2007 | Tran | A61B 5/0022 600/508 |
| 2010/0081901 | A1 | * | 4/2010 | Buice | A61B 5/14551 600/324 |
| 2014/0275928 | A1 | * | 9/2014 | Acquista | A61N 1/36585 600/382 |

(Continued)

*Primary Examiner* — Chu Chuan Liu
(74) *Attorney, Agent, or Firm* — Hogan Lovells US LLP

(57) ABSTRACT

Systems and devices of the present disclosure provide automated detection and tracking of carbon monoxide inhalation through non-invasive optical spectroscopy. A wearable device includes a light source coupled to the base and directing light towards a subject and a photodetector coupled to the base to receive light emitted by the light source through or reflected the subject. The light source emits light at a wavelength spectrum corresponding to a carboxyhemoglobin absorption spectrum and an oxyhemoglobin absorption spectrum. Biometric circuitry is coupled to the photodetector to receive a signal from the photodetector and process the signal to determine an intensity of the wavelengths present in the light received at the photodetector. The intensity of the wavelengths is indicative of a level of carbon monoxide inhalation associated with the subject.

19 Claims, 7 Drawing Sheets

(56) References Cited

U.S. PATENT DOCUMENTS

2014/0288390 A1* 9/2014 Hong ................. A61B 5/02427
                                                        600/301
2016/0022223 A1* 1/2016 Grundfest ............ A61B 5/0062
                                                        600/324

* cited by examiner

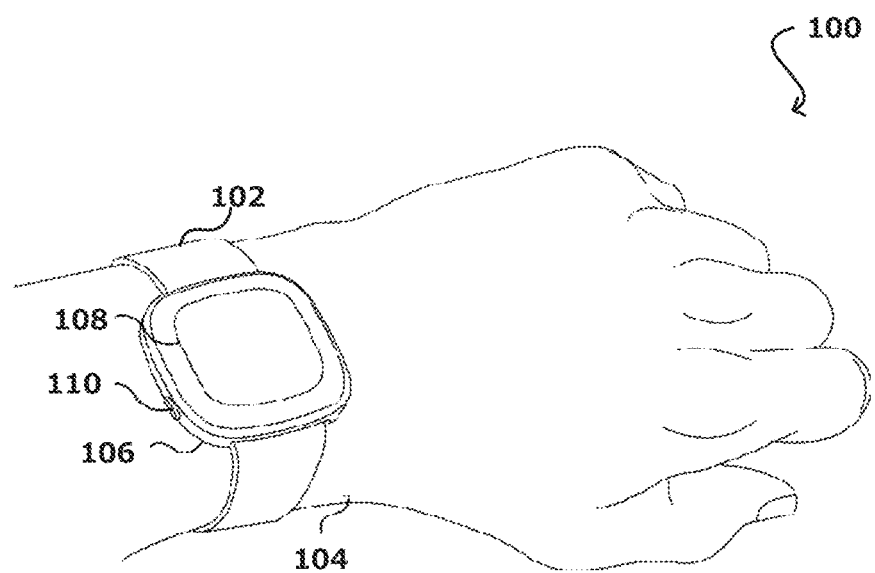
FIG. 3
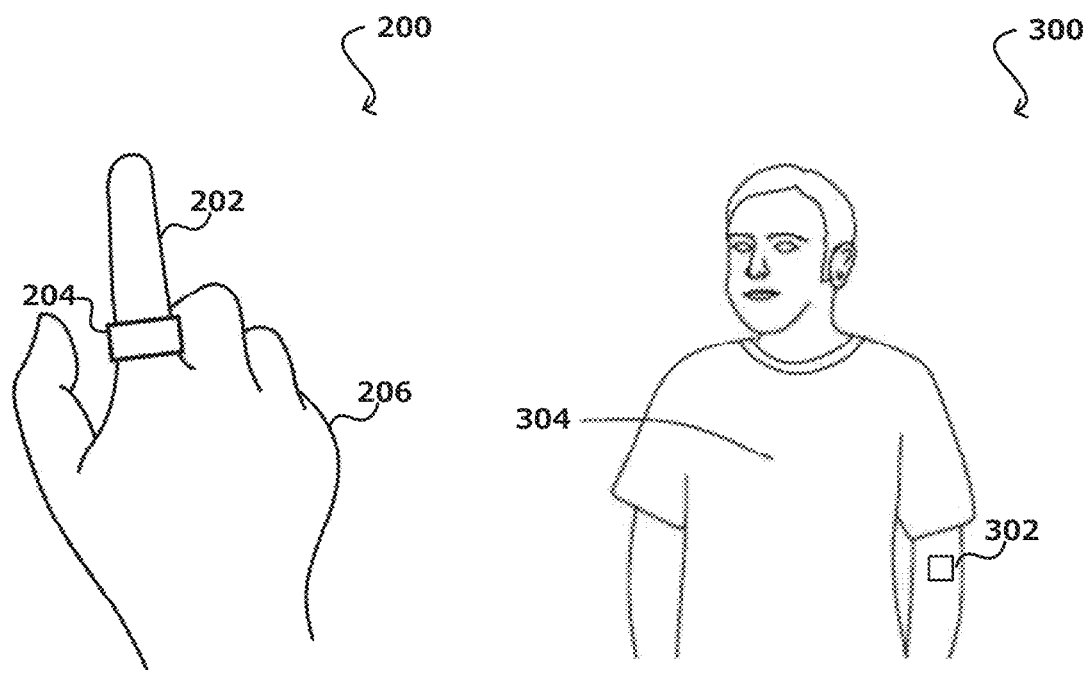
FIG. 1
FIG. 2

US 10,966,643 B1

WEARABLE NON-INVASIVE CARBON MONOXIDE INHALATION TRACKING

BACKGROUND

Recent advances in technology, including those available through consumer devices, have provided for corresponding advances in health detection and monitoring. For example, devices such as fitness bands and smart watches are able to determine information relating to the pulse or motion of a person wearing the device. Due to capabilities of conventional devices, however, the amount and types of health information able to be determined using such devices has been limited. Accordingly, much tracking or health monitoring done using these devices relies primarily upon user input. For example, individuals and healthcare providers may be interested in tracking the individual's smoking behavior or objectively tracking their progress while attempting to quit or reduce smoking. However, self-reporting of smoking behavior may be an unreliable metric, as well as being tedious and cumbersome for the individual.

BRIEF DESCRIPTION OF THE DRAWINGS

Various embodiments in accordance with the present disclosure will be described with reference to the drawings, in which:

FIG. 1 illustrates an example of a user wearing a monitoring device with carbon monoxide inhalation monitoring around a wrist of the user.

FIG. 2 illustrates a user wearing an example ring with carbon monoxide inhalation monitoring, according to various embodiments.

FIG. 3 illustrates an example of a user using patch with carbon monoxide inhalation monitoring, in accordance with example embodiments.

DETAILED DESCRIPTION

Figure 4:
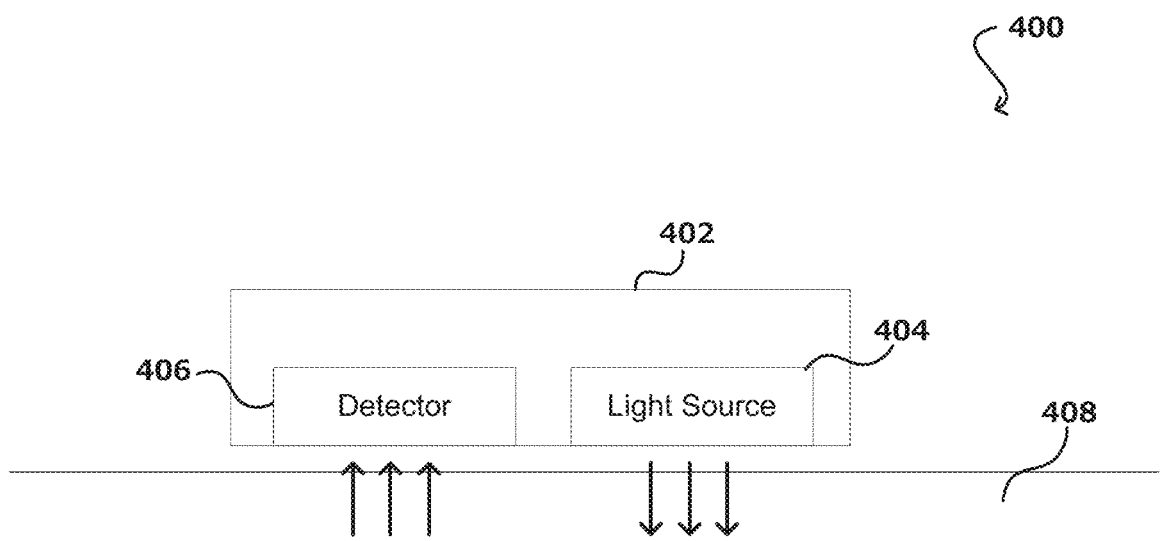
FIG. 4 illustrates an embodiment utilizing reflective light detection, in accordance with example embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Approaches in accordance with various embodiments provide for automated health monitoring, and in particular relate to the automated detection and tracking of carbon monoxide inhalation through non-invasive optical spectroscopy. In some embodiments, a wearable device such as a ring, watch, or patch, among others, may include an optical based carbon monoxide inhalation detection system. The detection system utilizes non-invasive optical spectroscopy to detect for the presence of carboxyhemoglobin in the blood of the user. The detection system may also measure the presence of oxyhemoglobin in the blood. Oxyhemoglobin is formed when hemoglobin contacts oxygen. Carboxyhemoglobin is a stable complex of carbon monoxide and hemoglobin that forms in red blood cells upon contact with carbon monoxide such as when carbon monoxide is inhaled. This makes carboxyhemoglobin a good indicator of carbon monoxide inhalation.

In some embodiments, the wearable device includes an attachment mechanism for attaching the monitoring device to a subject and a base coupled to the attachment mechanism. For example, the attachment mechanism may be a strap, a ring, an adhesive material, among others. The base may be an underside of a watch face, an inner surface of a ring, or an adhesive side of a patch, that is in contact with the user. A light source, which can be a single light source or made up of multiple light sources, is coupled to the base and directs a light into the subject. In some embodiments, the light source may include a narrow band light sources that correspond to the carboxyhemoglobin absorption spectrum, approximately 550-580 nm. In some embodiments, the light source may correspond to a portion of the 550-580 nm spectrum rather than the entire range. The light source may also include a narrow band light source that corresponds to the oxyhemoglobin absorption spectrum, approximately 530-540 nm. Thus the light emitted from the light source may include light of both wavelength ranges. The narrow band light sources could include lasers, resonant cavity LEDs, or optically filtered conventional LEDs, for example. The light source could also include other visible and/or infrared wavelengths to provide a baseline for tissue optical properties and/or blood concentration. This baseline could be used to improve the carboxyhemoglobin reading.

The light emitted from the light source travels into the user's body, where a portion of the light may be transmitted through or reflected out, or both. Thus, a photodetector of the wearable device, which can be a single detector or made up of multiple detectors, is positioned to receive the light that has traveled through the subject's tissue. The received light is then analyzed to generate certain biometric signals. Specifically, the light is analyzed to determine different wavelengths present in the light. Since the light emitted into the subject tissue included light in the carboxyhemoglobin wavelength spectrum and light in the carboxyhemoglobin wavelength spectrum, the attenuation of light in the carboxyhemoglobin spectrum detected at the photodetector indicates the presence of carboxyhemoglobin, as some of the light was absorbed by the carboxyhemoglobin. Similarly, the attenuation of light in the oxyhemoglobin spectrum detected at the photodetector indicates the presence of oxyhemoglobin, as some of the light was absorbed by the oxyhemoglobin. A carboxyhemoglobin signal can be generated from the amount of attenuation of light in the carboxyhemoglobin spectrum, which may indicate an amount of carboxyhemoglobin in the blood. Likewise, an oxyhemoglobin signal can be generated based on the amount of attenuation of light in the oxyhemoglobin spectrum, which may indicate an amount of oxyhemoglobin in the blood. In some embodiments, the ratio between the carboxyhemoglobin signal and the oxyhemoglobin signal may be used to make certain determination about monoxide inhalation by the user.

In some embodiments, the measurements and calculations determined at the wearable device may be communicated to a remote device, such as a smartphone, a computer, a monitoring device, of other multi-purpose of specialized device. The data may be further analyzed at the remoted device, logged, correlated with other data, further communicated, or used to generate alarms or notifications. In some embodiments, various data processing, interpretation, and action triggers may be performed at the wearable device, the remote device, or both. Various other functions can be implemented within the various embodiments as well as discussed and suggested elsewhere herein.

For various reasons, it can be desirable to track the inhalation of carbon monoxide in an automated and non-invasive fashion, whether the inhalation is from intentional smoking or environmental conditions. It can also be desirable that such tracking can be performed with minimal intervention required by the user. Some conventional approaches to tracking smoking rely on manual entry or annotation by an individual. Some other previous approaches have used respiration-detecting bands around the torso, which are uncomfortable and prone to false reporting. Attempting to track smoking-specific motions with accelerometers may not pick up anything if the user is wearing the sensor on the hand opposite the hand holding the cigarette. The system and techniques of the present disclosure directly tracks systemic blood chemistry changes that occur as a result of carbon monoxide inhalation, rather than relying on self-reporting and secondary signals just as respiration rate or hand motions. A wearable sensor that tracks changes in the user's body has the further advantage of traveling with the user organically, which facilitates ease and likelihood of adherence.

FIG. 1 illustrates an example of a user 100 wearing a monitoring device 102 with carbon monoxide inhalation monitoring around a wrist 104 of the user 100. The user monitoring device 102 may also be referred to as a wearable or a fitness tracker, and may also include devices that are worn around the chest, legs, head, or other body part, or a device to be clipped or otherwise attached onto an article of clothing worn by the user 100. As described in further detail below with respect to FIGS. 4 and 5, the monitoring device 102 includes a non-invasive optical spectroscopy system for carbon monoxide inhalation monitoring. The optical spectroscopy system includes a light source and a photodetector located at a base 106 of the device 102 wherein the device 102 contacts the user 200. The system also includes processing circuitry capable of detecting the presence of carboxyhemoglobin in the blood of the user using non-invasively optical spectroscopy. The presence and amount of carboxyhemoglobin can provide an indication of recent smoking behavior or other forms of carbon monoxide inhalation. For example, the measurements made by the monitoring device 102 may indicate how much the user has smoked, their frequency and duration of smoking, and the like. It may also detect carbon monoxide poisoning, increased carbon monoxide inhalation, and generate alerts accordingly.

The user monitoring device 102 includes a user interface that may include a display 108 and a button 110. Additionally, the user monitoring device 102 may collectively or respectively capture data related to any one or more of caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, respiration rate and patterns, various body movements, among others. Additional data may be provided from an external source, e.g., the user may input their height, weight, age, stride, or other data in a user profile on a fitness-tracking website or application and such information may be used in combination with some of the above-described data to make certain evaluation or in determining user behaviors, such as the distance traveled or calories burned of the user. The user monitoring devices may also measure or calculate metrics related to the environment around the user such as barometric pressure, weather conditions, light exposure, noise exposure, and magnetic field. One or more these example measurements may be used in correlation with the carbon monoxide monitoring to provide more insightful data and a fuller picture of the user's various conditions and overall wellbeing. Different types of measurements may be used to corroborate each other, remove false negatives and false positives, and the like. For example, since the device 102 is worn on the wrist, an accelerometer in the device 102 may be able to detect a certain whist motion that is associated with smoking actions, (e.g., a certain up and down motion). This data combined with the carbon monoxide inhalation data may be able to more accurate pin point the time and duration of when the user was smoking. In another example, the device 102 may track the GPS coordinates of the user, and if an unsafe level of carbon monoxide poisoning is detected, an alert may be sent to a third party along with the GPS coordinates of the user so that assistance may arrive quickly.

In some embodiments, the user monitoring device 102 may be connected to a network directly, or via an intermediary device. For example, the use monitoring device 102 may be connected to the intermediary device such as a smartphone, and the intermediary device may be connected to the network via an Internet connection. In various embodiments, a user may be associated with a user account, and the user account may be associated with (i.e., signed onto) a plurality of different networked devices. In some embodiments, additional devices may provide any of the abovementioned data among other data, and/or receive the data for various processing or analysis. The additional devices may include a computer, a server, a handheld device, a temperature regulation device, or a vehicle, among others.

FIG. 2 illustrates a user 200 wearing an example ring 204 with carbon monoxide inhalation monitoring, according to various embodiments. For example, a user can wear the ring 204 on a finger 202 of the user's hand. The user can then connect to the ring 204 with a remote portable electronic device such as a phone or watch. The ring 204 can collect biometric data and periodically send the data to the portable electronic device for processing, display, and/or retransmission to a networked service. The carbon monoxide inhalation monitoring functions of ring 204 may be similar to that described above with respect to the device 102 of FIG. 1. According, the ring 204 includes a light source and a photodetector located on an inner side where the ring 204 contacts the user. The ring 204 includes processing circuitry capable of detecting the presence of carboxyhemoglobin in the blood of the user using non-invasively optical spectroscopy. The ring 204 may also include any of the devices and functionality described above with respect to the device 102 of FIG. 1, as well as additional devices and functionality. The ring 204 can implement power saving measures to prolong the battery life. The ring 204 can generally be in a low power state unless it is measuring data or transmitting data to another device, thus extending the battery life in comparison to traditional approaches. The battery life can be a few days to a number of weeks depending on use.

FIG. 3 illustrates an example of a user 300 using patch 302 with carbon monoxide inhalation monitoring, in accordance with example embodiments. The patch 302 may be applied or coupled directly to the user's body 304, and may be self-adhesive. FIG. 3 illustrates the patch 302 as being applied to the user's arm 304. However, the patch 302 may be applied to a number of different regions on the user's body, such as the head, leg, chest, stomach region, etc. Similar to the example wearables illustrated in FIGS. 2 and 3, the patch includes a light source, a photodetector, and processing circuitry capable of detecting the presence of carboxyhemoglobin in the blood of the user using non-invasively optical spectroscopy. The patch may include various components capable of measuring various physiological aspects of the user such as various other blood chemistry, movement, respiration, among others. In some embodiments, the patch 302 may be connected to a network directly, or via an intermediary device. For example, the patch 302 may be connected to the intermediary device via a Bluetooth connection, and the intermediary device may be connected to the network via an Internet connection. In various embodiments, the user 300 may be associated with a user account, and the user account may be associated with (i.e., signed onto) a plurality of different networked devices. In some embodiments, additional devices may provide any of the abovementioned data among other data, and/or receive the data for various processing or analysis. The additional devices may include a computer, a server, a handheld device, a wearable device, among others. Additional data may also be provided and used to further process or interpret the results.

It should be understood that the principles herein disclosed herein can be implemented in other device forms in addition to the example wearable forms described above with respect to the watch, ring, and patch. For example, an earring can be worn on a user's earlobe and can shine a light through the lobe for detection on the other side of the ear. The principles can also apply to a navel ring, nose ring, anklet, bracelet, etc. In some embodiments, the principles herein disclosed can be applied to a glove (e.g., a photodetector can be on one side of the glove and a light source can be on the other side; light can then be passed through the palm of the gloved hand). Similarly, the principles herein can be applied to a shoe or sock whereby a light source can shine light through a toe or arch of a person's foot. Motion artifacts often present a challenge to wearable measurements of blood analytes. In order to avoid motion artifacts, accelerometer data may be used to filter out time periods that correspond to high motion.

As mentioned, the various embodiments can be implemented as a system that includes one or more tracking devices for a given user. In other embodiments the embodiments may be provided as a service, which users can utilize for their devices. Other tracker providers may also subscribe or utilize such a service for their customers. In some embodiments an application programming interface (API) or other such interface may be exposed that enables collected body data, and other information, to be received to the service, which can process the information and send the results back down to the tracker, or related computing device, for access by the user. In some embodiments at least some of the processing may be done on the tracking or computing device itself, but processing by a remote system or service may allow for more robust processing, particularly for tracking devices with limited capacity or processing capability.

Figure 5:
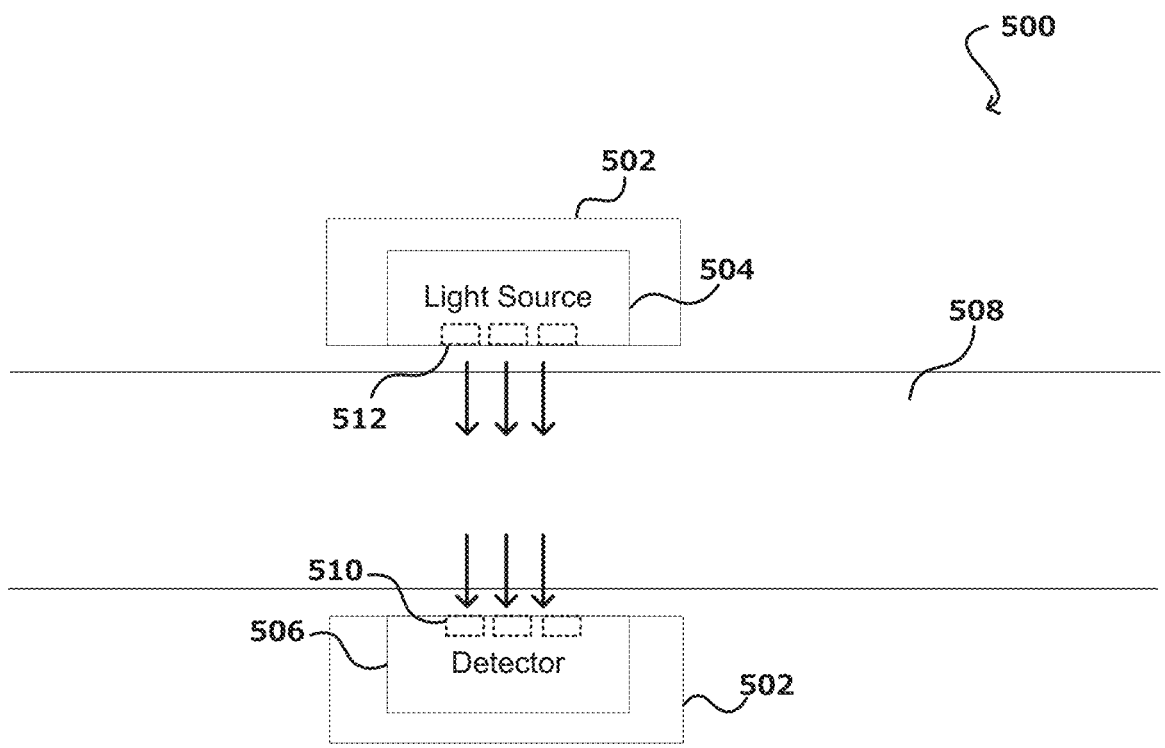
FIG. 5 illustrates an embodiment of a carbon monoxide inhalation monitoring system utilizing transmissive light detection, in accordance with example embodiments.

FIGS. 4 and 5 illustrate representations of components of a carbon monoxide inhalation monitoring system 400, in accordance with example embodiments. A carbon monoxide inhalation monitoring system can be implemented on any of the above example wearable types, among many others, to monitor carboxyhemoglobin and oxyhemoglobin levels of a user. Additionally, in some embodiments, many other physiological conditions may be monitored as well, including pulse, blood pressure, glucose levels, lipid concentration, movement, among others. These measurements can largely be taken by measuring the transmission and/or reflection of light through a user's finger. FIG. 4 illustrates an embodiment utilizing reflective light detection, in accordance with example embodiments. Referring to FIG. 4, the system 400 includes a housing 402 (e.g., base or substrate), a light source 404, and a photodetector 406. The light source 404 emits light into the body tissue 408 (e.g., blood) of a user. The light source 404 is positioned substantially on the same side of the tissue as the photodetector 406. For example, the light source 404 can be positioned next to the photodetector 406. This can facilitate reflective readings of the light that reflects off the interior of the finger.

The light source 404 may include various types of lighting device, such as a light emitting diode (LED). The light source 404 can be used which emits a certain primary wavelength of light. The light source 404 may be coupled to a base or user contact surface of the wearable or monitoring device. For example, the base may be an underside of a watch face, an inner surface of a ring, or an adhesive side of a patch, that is in contact with the user. A light source 404 can be used which emits light according to a wide range of wavelengths (e.g., "white" light that mimics natural sunlight). In some embodiments, one or more filters can be placed on a light source 404 to limit the wavelengths of transmission. In some embodiments, multiple light sources 404 can be independently activated. For example, a red LED can be activated and then an ultraviolet LED can subsequently be activated. In some embodiments, light guides can provide the light from a single light source 404 to various locations on the wearable device. In some embodiments, ambient light can be utilized as the light source 404. For example, the wearable device can detect ambient light that passes at least partially through the tissue 408 of the user. Other external light sources may be utilized as well.

The light emitted is inclusive of a wavelengths corresponding to a carboxyhemoglobin wavelength spectrum, an oxyhemoglobin wavelength spectrum, and a deoxyhemoglobin wavelength spectrum. Depending on the types and amounts of analytes present in the tissue 408, some of the light may be absorbed by the analytes, and the remaining light is reflected back out and detected at the photodetector 406. Based on which wavelengths of light are absorbed by the finger and thus attenuated, the system can determine the carboxyhemoglobin and oxyhemoglobin levels in the user's body. Specifically, the detection system utilizes non-invasive optical spectroscopy to detect for the presence of carboxyhemoglobin in the blood of the user. The detection system may similarly measure the presence of oxyhemoglobin and deoxyhemoglobin in the blood.

In some embodiments, the light source 404 may include a narrow band light sources that correspond to the carboxyhemoglobin absorption spectrum, approximately 550-580 nm. The light source 404 may also include a narrow band light source that corresponds to the oxyhemoglobin absorption spectrum, approximately 530-540 nm. Thus the light emitted from the light source may include light of both wavelength ranges. The narrow band light sources could include lasers, resonant cavity LEDs, or optically filtered conventional LEDs, for example. In some embodiments, the light source 404 may be a full-spectrum source, and the light is spectrally resolved at the photodetector 406.

The photodetector 406 may include a photodiode and/or phototransistor to detect the amount of light that passes through a tissue 408. The photodetector 406 can detect light reflected within the tissue and/or transmitted through the tissue. In some embodiments, a photodetector 406 can be configured for a particular wavelength of light such as red or infrared light. In some embodiments, a photodetector 406 can have a filter configured to permit the particular wavelength to pass. In some embodiments, the photodetector 406 is not configured for a single wavelength of light but can be activated by multiple wavelengths of light. Such a configuration can be useful when multiple light sources 406 are used with corresponding wavelengths. The light emitted from the light source 404 travels into the tissue 408, where a portion of the light may be transmitted through or reflected out, or both. Thus, the photodetector 406 of the wearable device is positioned to receive the light that has traveled through the tissue.

FIG. 5 illustrates an embodiment of a carbon monoxide inhalation monitoring system 500 utilizing transmissive light detection, in accordance with example embodiments. Similarly, the system includes a housing 502, a light source 504, and a detector 506. The light source 504 is positioned largely opposite of the photodetector 506 as shown in FIG. 5. This can facilitate transmissive readings of light that passes through the tissue. In some embodiments, the placement of the light source 504 relative to the photodetector 506 can be varied to obtain a blend of transmissive and reflective readings. In some embodiments, the light source 504 may include multiple light emitting devices 510 and the photodetector 506 may include multiple photodetector devices 512. Furthermore, it should be understood that a single photodetector 506 can be used to take readings from various light sources 504 and a single light source 504 can provide light to multiple photodetectors 506.

In both the transmissive and reflective detection embodiments, the light received at the photodetector is then analyzed to generate certain biometric information. Specifically, the light is analyzed to determine different wavelengths present in the light. Since the light emitted into the subject tissue included light in the carboxyhemoglobin wavelength spectrum and light in the carboxyhemoglobin wavelength spectrum, the attenuation of light in the carboxyhemoglobin spectrum detected at the photodetector indicates the presence of carboxyhemoglobin, as some of the light was absorbed by the carboxyhemoglobin. Similarly, the attenuation of light in the oxyhemoglobin spectrum detected at the photodetector indicates the presence of oxyhemoglobin, as some of the light was absorbed by the oxyhemoglobin. A carboxyhemoglobin signal can be generated from the amount of attenuation of light in the carboxyhemoglobin spectrum, which may indicate an amount of carboxyhemoglobin in the blood. Likewise, an oxyhemoglobin signal can be generated based on the amount of attenuation of light in the oxyhemoglobin spectrum, which may indicate an amount of oxyhemoglobin in the blood. In some embodiments, the ratio between the carboxyhemoglobin signal and the oxyhemoglobin signal may be used to make certain determination about monoxide inhalation by the user. In some embodiments, once increases in relative carboxyhemoglobin blood fraction are measured, they could be compared against a threshold and time-varying waveform template to determine a smoking event. Multi-variate or machine learning algorithms could determine a smoking event based on many features derived from accelerometer and optical sensor data. Once a smoking event was determined, the wearable device could store the time of each event, and upload it to a data repository for later display to the user, healthcare provider or health insurance provider. The amount of smoking (e.g., number of cigarettes) may be determined based on the magnitude of the increase.

In some embodiments, the measurements and calculations determined at the wearable device may be communicated to a remote device, such as a smartphone, a computer, a monitoring device, of other multi-purpose of specialized device. The data may be further analyzed at the remote device, logged, correlated with other data, further communicated, or used to generate alarms or notifications. In some embodiments, various data processing, interpretation, and action triggers may be performed at the wearable device, the remote device, or both. Various other functions can be implemented within the various embodiments as well as discussed and suggested elsewhere herein.

Figure 6:
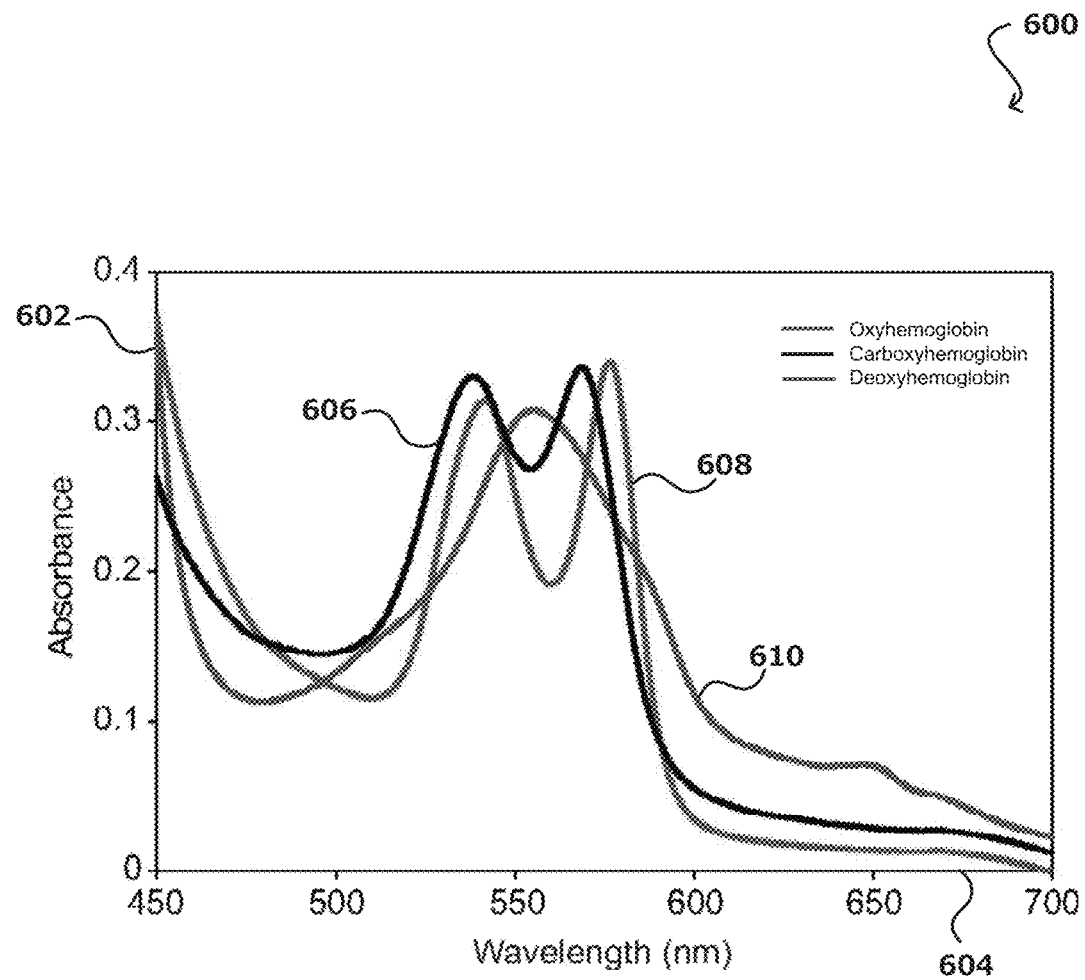
FIG. 6 is a graph illustrating relevant absorption wavelengths for carbon monoxide inhalation detection, in accordance with example embodiments.

FIG. 6 is a graph 600 illustrating relevant absorption wavelengths for carboxyhemoglobin detection, in accordance with example embodiments. Specifically, the graph 600 shows the wavelength 602 to absorbance 604 for carboxyhemoglobin 606, oxyhemoglobin 608, and deoxyhemoglobin 610. The presence of carboxyhemoglobin, oxyhemoglobin and deoxyghemoglobin in the blood can be distinguished from each other by using one or more narrow band light sources to look for the carboxyhemoglobin absorption peak at a wavelength of around 570 nm, which is distinct from the oxyhemoglobin peak that occurs at a slightly longer wavelength. In some embodiments, measurements can be taken at other reference wavelengths such as 660 nm to estimate the ratio of carboxyhemoglobin to other hemoglobin species based on the ratios of light transmitted at these wavelengths. In some embodiments, the light source may emit light having a wavelength band of approximately 550 nm-580 nm, in order to obtain measurements of carboxyhemoglobin. The light source may emit light having a wavelength band of approximately 530 nm-540 nm, in order to obtain measurements of oxyhemoglobin.

Since the light emitted into the subject tissue included light in the carboxyhemoglobin wavelength spectrum and light in the oxyhemoglobin wavelength spectrum, the attenuation of light in the carboxyhemoglobin spectrum detected at the photodetector indicates the presence of carboxyhemoglobin, as some of the light was absorbed by the carboxyhemoglobin. Similarly, the attenuation of light in the oxyhemoglobin spectrum detected at the photodetector indicates the presence of oxyhemoglobin, as some of the light was absorbed by the oxyhemoglobin. A carboxyhemoglobin signal can be generated from the amount of attenuation of light in the carboxyhemoglobin spectrum, which may indicate an amount of carboxyhemoglobin in the blood. Likewise, an oxyhemoglobin signal can be generated based on the amount of attenuation of light in the oxyhemoglobin spectrum, which may indicate an amount of oxyhemoglobin in the blood. In some embodiments, the ratio between the carboxyhemoglobin signal and the oxyhemoglobin signal may be used to make certain determinations about monoxide inhalation by the user.

In some embodiments, in order to determine the light attenuation measurement at each wavelength band, a single light source and single detector separated by a distance may be utilized. In some embodiments, multiple measurements may be taken at different distances between one or more light sources and one or more detectors, in order to add some resolution of depth within the skin/tissue to the measurements and also to factor out common artifacts at the surface of the skin. In some embodiments in order to estimate relative carboxyhemoglobin, the system can be configured to measure either the non-pulsatile DC light signal or the pulsatile signal to isolate the measurement to pulsating arteries. In some embodiments, a combination of both signals may be used.

Figure 7:
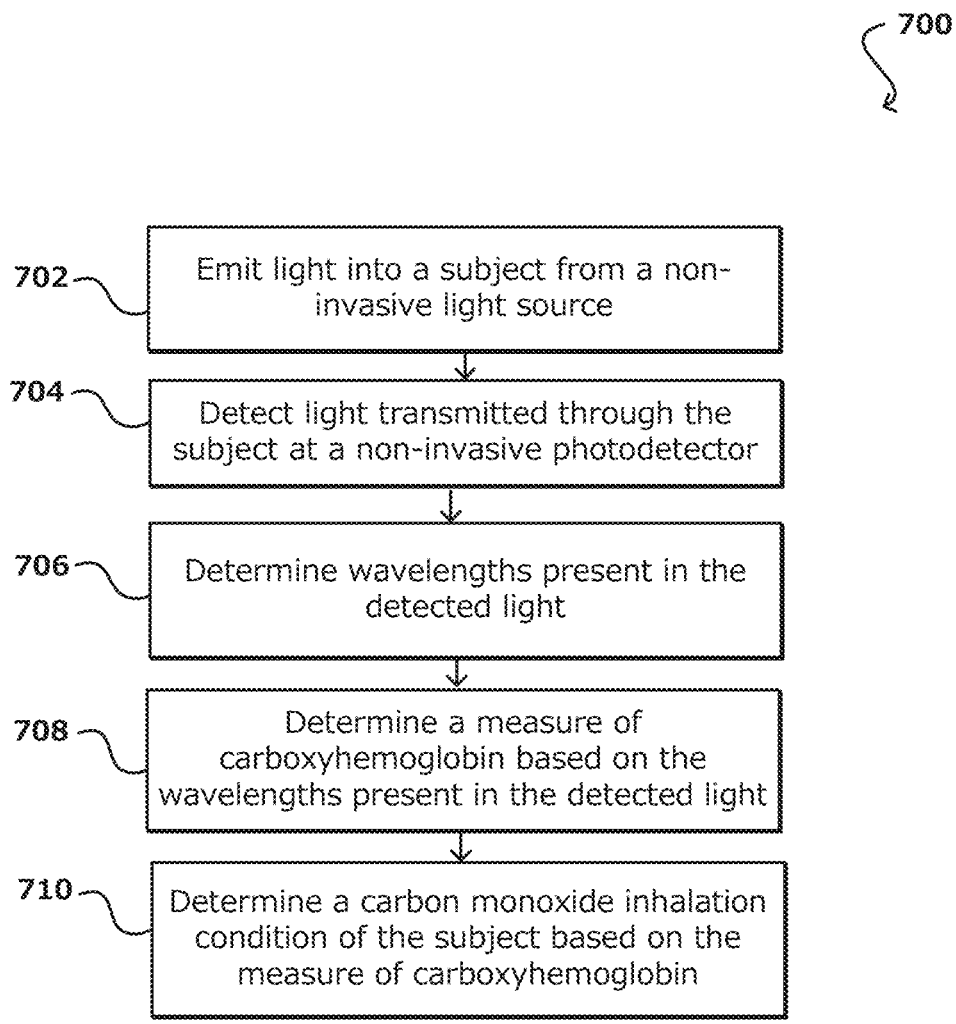
FIG. 7 is a flowchart of an example process for performing carbon monoxide inhalation monitoring, in accordance with some example embodiments.

FIG. 7 is a flowchart of an example process 700 for performing carbon monoxide inhalation monitoring, in accordance with some example embodiments. It should be understood that, for any process discussed herein, there can be additional, fewer, or alternative steps performed in similar or alternative orders, or in parallel, within the scope of the various embodiments. In this example, light is emitted from a non-invasive light source into the skin/tissue of a subject (e.g., a user wearing the device). In this example, light is emitted 702 from a light source of a wearable carbon monoxide inhalation monitoring device into the skin/tissue of a subject (e.g., the user wearing the wearable device). The light source is located external to the subject and is thus non-invasive. For example, the light source may be on an inner surface of a ring worn around the finger of the subject, and light from the light source is directed into the finger of the subject. In some embodiments, the light source may be external to the device, such as ambient light, and the device directs the light towards the subject.

The light travels at part partially into the tissue of the subject and transmitted through or reflected out via one or more structures in the tissue. The light is then detected 704 at a non-invasive photodetector. For example, the photodetector may also be located on the inner surface of the ring. The detected light is analyzed to determine 706 wavelengths present in the light. A measure of carboxyhemoglobin can be determined 708 based on the wavelengths present in the detected light. Specifically, since the light emitted into the subject tissue included light in the carboxyhemoglobin wavelength spectrum and light in the carboxyhemoglobin wavelength spectrum, the attenuation of light in the carboxyhemoglobin spectrum detected at the photodetector indicates the presence of carboxyhemoglobin, as some of the light was absorbed by the carboxyhemoglobin. A carboxyhemoglobin signal can be generated from the amount of attenuation of light in the carboxyhemoglobin spectrum, which may indicate an amount of carboxyhemoglobin in the blood. The presence of carboxyhemoglobin in the blood is indicative of and directly correlated with carbon monoxide inhalation. Thus, a carbon monoxide inhalation condition can be determined 710 based at least in part on the measure of carboxyhemoglobin. In some embodiments, the light emitted from the light source is a full spectrum light, and the received light is spectrally resolved at the photodetector. In some other embodiments, the light source includes a one or more light sources of different narrow band wavelengths corresponding to the carboxyhemoglobin, oxyhemoglobin, and/or deoxyhemoglobin. The light may be emitted and/or detected continuously or intermittently over a period of time. The measures of carboxyhemoglobin, oxyhemoglobin, and/or deoxyhemoglobin made over the period of time may be averaged or viewed over time.

In some embodiments, the device includes biometric circuitry coupled to the photodetector to receive a signal from the photodetector and process the signal to determine an intensity of the wavelengths present in the light received at the photodetector, in which the intensity of the wavelengths is indicative of a level of carbon monoxide inhalation associated with the subject. In some embodiments, a raw data signal from the photodetector or a minimally processed signal may be transmitted from the wearable to another user device where such analysis may be performed.

Figure 8:
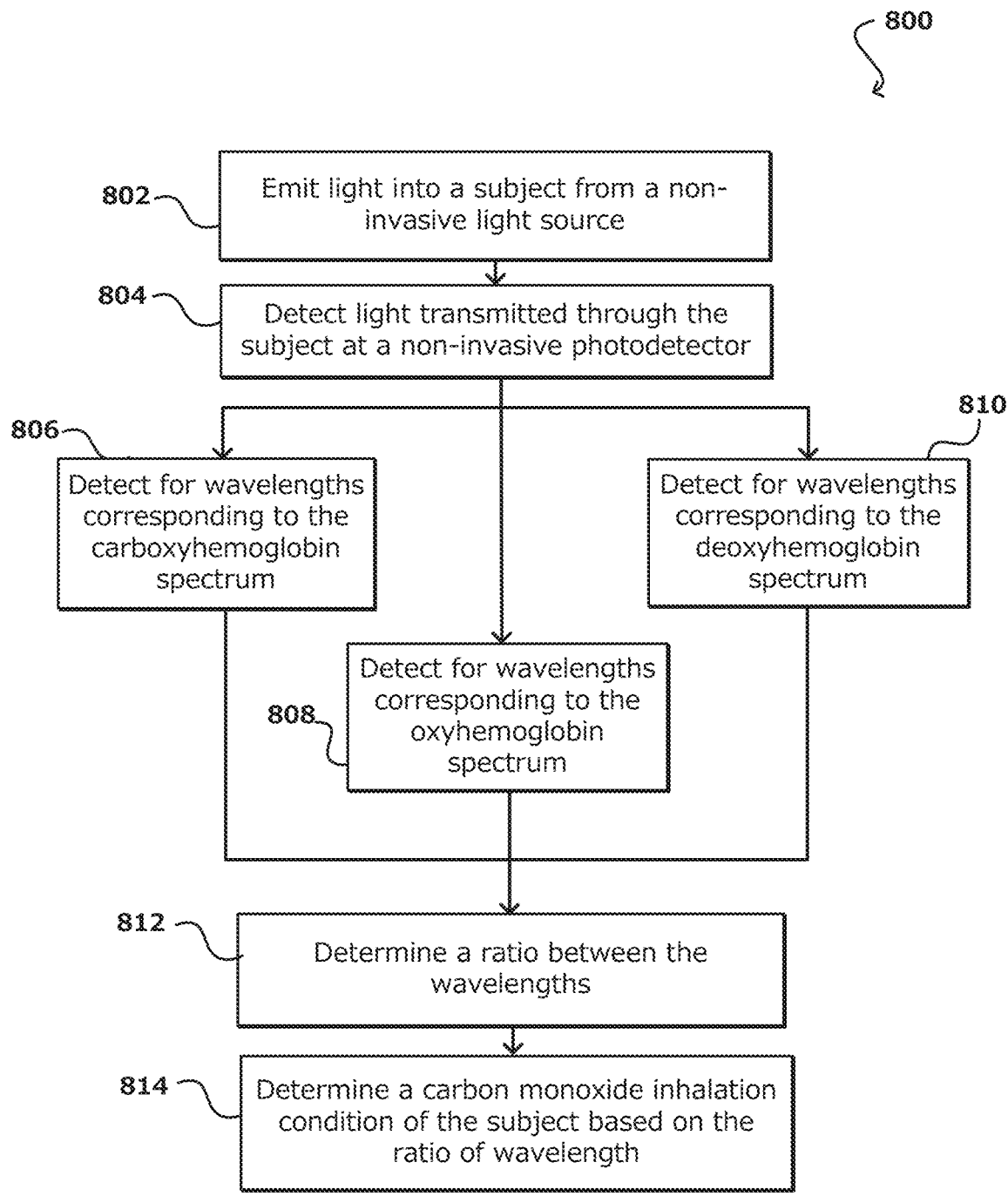
FIG. 8 is a flowchart of an example process for performing carbon monoxide inhalation monitoring, in accordance with some example embodiments.

FIG. 8 is a flowchart of an example process 800 for performing carbon monoxide inhalation monitoring, in accordance with some example embodiments. In this example, light is emitted 802 from a light source of a wearable carbon monoxide inhalation monitoring device into the skin/tissue of a subject (e.g., the user wearing the wearable device). The light is then detected 904 at a non-invasive photodetector. The received light is used to detect 806 for wavelengths corresponding to the above-described carboxyhemoglobin spectrum, in order to determine presence of carboxyhemoglobin in the subject. Similarly, the received light is used to detect 808 for wavelengths corresponding to the above-described oxyhemoglobin spectrum, in order to determine presence of oxyhemoglobin in the subject. The received light can also be used to detect 810 for wavelengths corresponding to the above-described deoxyhemoglobin spectrum, in order to determine presence of deoxyhemoglobin in the subject. A ratio of these wavelengths detected in the received light is then determined 812. This ratio may be used to determine 814 a carbon monoxide inhalation condition of the subject.

Figure 9:
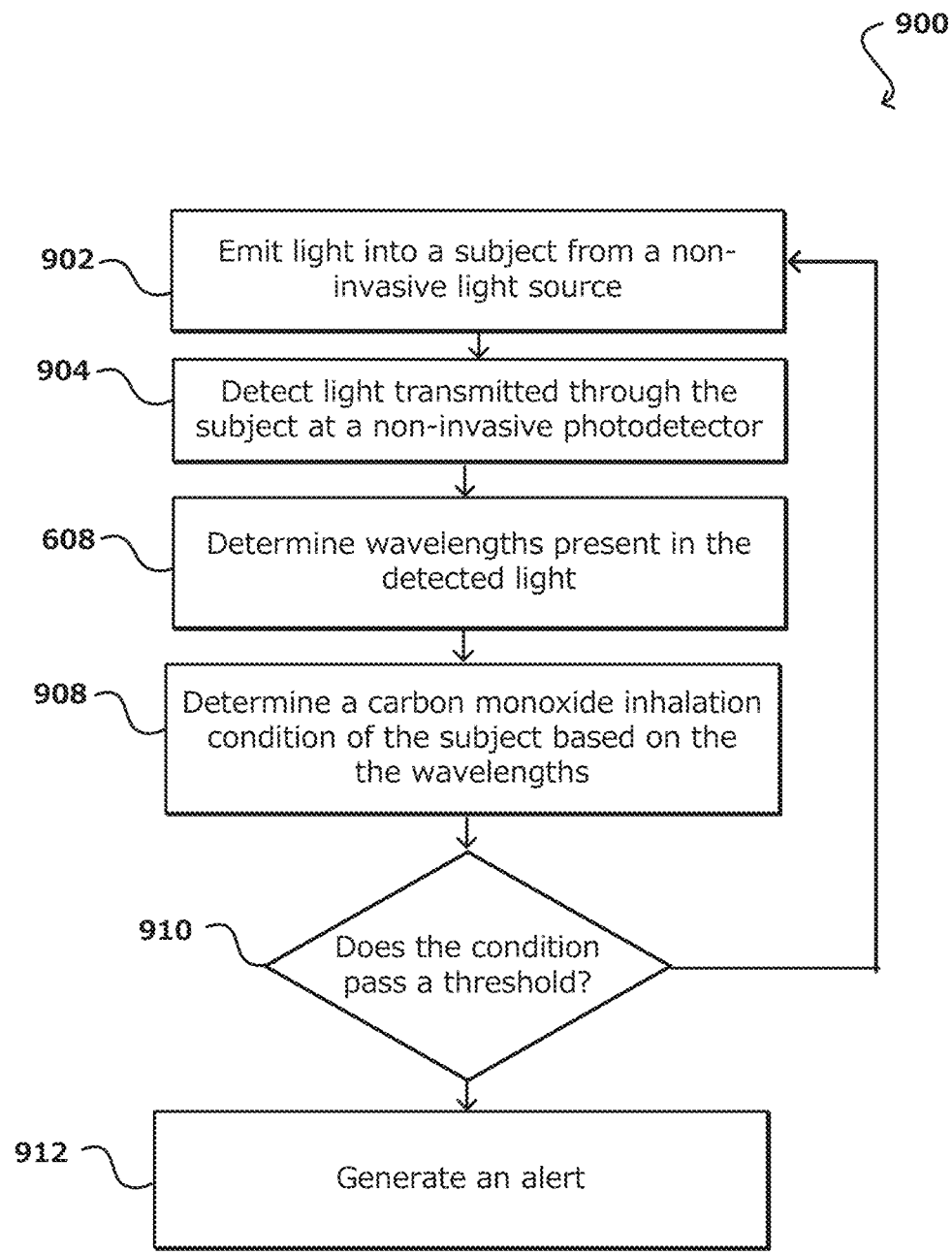
FIG. 9 is a flowchart of an example process for performing carbon monoxide inhalation monitoring, in accordance with some example embodiments.

FIG. 9 is a flowchart of an example process 900 for performing carbon monoxide inhalation monitoring, in accordance with some example embodiments. In this example, light is emitted 902 from a light source of a wearable carbon monoxide inhalation monitoring device into the skin/tissue of a subject (e.g., the user wearing the wearable device). The light source is located external to the subject and is thus non-invasive. For example, the light source may be on an inner surface of a ring worn around the finger of the subject, and light from the light source is directed into the finger of the subject. The light travels at part partially into the tissue of the subject and transmitted through or reflected out via one or more structures in the tissue. The light is then detected 904 at a non-invasive photodetector. For example, the photodetector may also be located on the inner surface of the ring.

The light detected at the photodetector is then analyzed to determine 906 the wavelengths present in the received light. Since the light emitted into the subject tissue included light in the carboxyhemoglobin wavelength spectrum and light in the carboxyhemoglobin wavelength spectrum, the attenuation of light in the carboxyhemoglobin spectrum detected at the photodetector indicates the presence of carboxyhemoglobin, as some of the light was absorbed by the carboxyhemoglobin. Similarly, the attenuation of light in the oxyhemoglobin spectrum detected at the photodetector indicates the presence of oxyhemoglobin, as some of the light was absorbed by the oxyhemoglobin. A carboxyhemoglobin signal can be generated from the amount of attenuation of light in the carboxyhemoglobin spectrum, which may indicate an amount of carboxyhemoglobin in the blood. Likewise, an oxyhemoglobin signal can be generated based on the amount of attenuation of light in the oxyhemoglobin spectrum, which may indicate an amount of oxyhemoglobin in the blood. Thus, a carbon monoxide inhalation condition of the subject may be determined 908 based on the wavelengths detects in the received light.

The determined carbon monoxide inhalation condition can be compared 910 to one or more thresholds to determine whether the carbon monoxide inhalation condition passes a threshold. If the carbon monoxide inhalation condition passes the threshold, an alert is generated 912. For example, an alert may appear on a user interface of a wearable or another device (e.g., smartphone) connected to the wearable. If the carbon monoxide inhalation condition does not pass the threshold, then the monitoring may resume.

Figure 10:
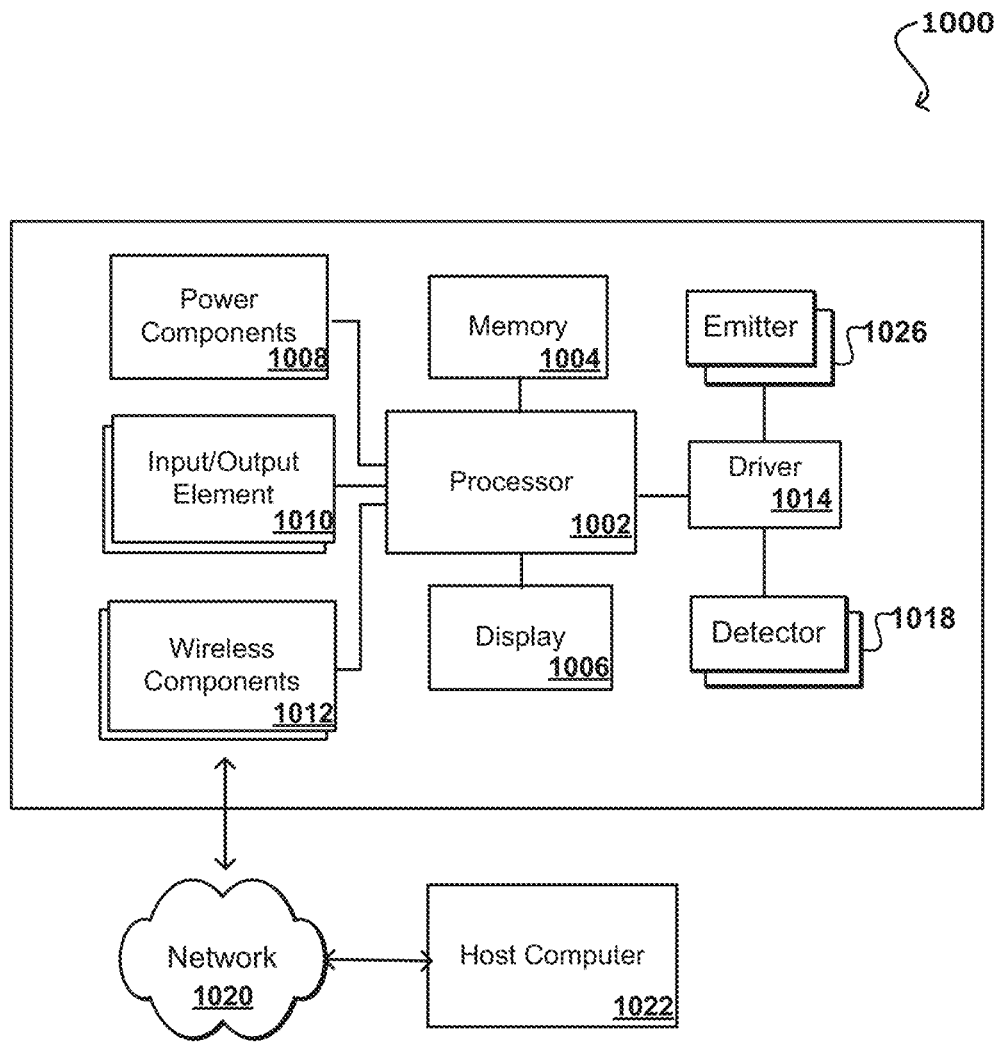
FIG. 10 illustrates components of an example user monitoring system with carbon monoxide inhalation monitoring that can be utilized in accordance with various embodiments.

FIG. 10 illustrates components of an example user monitoring system 1000 with carbon monoxide inhalation monitoring that can be utilized in accordance with various embodiments. In this example, the device includes at least one processor 1002, such as a central processing unit (CPU) or graphics processing unit (GPU) for executing instructions that can be stored in a memory device 1004, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data, a removable memory can be available for sharing information with other devices, and any number of communication approaches can be available for sharing with other devices. The device typically will include some type of display 1006, such as a touch screen, organic light emitting diode (OLED), or liquid crystal display (LCD), although devices might convey information via other means, such as through audio speakers or projectors.

A tracker or similar device will include at least one motion detection sensor, which as illustrated can include at least one I/O element 1010 of the device. Such a sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, motion along a non-linear path, etc.) of the device. An orientation determining element can also include an electronic or digital compass, which can indicate a direction (e.g., north or south) in which the device is determined to be pointing (e.g., with respect to a primary axis or other such aspect). A device may also include an I/O element 1010 for determining a location of the device (or the user of the device). Such a positioning element can include or comprise a GPS or similar location-determining element(s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers that enable the device to obtain the location information (e.g., by mapping the identifiers to a corresponding location). Various embodiments can include one or more such elements in any appropriate combination. The I/O elements may also include one or more biometric sensors, optical sensors, barometric sensors (e.g., altimeter, etc.), and the like.

As mentioned above, some embodiments use the element(s) to track the location and/or motion of a user. Upon determining an initial position of a device (e.g., using GPS), the device of some embodiments may keep track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 1012 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 1008, such as may include a battery operable to be recharged through conventional plug-in approaches, or through other approaches such as capacitive charging through proximity with a power mat or other such device. In some embodiments the device can include at least one additional input/output device 1010 able to receive conventional input from a user. This conventional input can include, for example, a push button, touch pad, touch screen, wheel, joystick, keyboard, mouse, keypad, or any other such device or element whereby a user can input a command to the device. These I/O devices could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 1016 and one or more detectors 1018 for measuring data for one or more metrics of a human body, such as for a person wearing the tracker device. In some embodiments this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device.

The example device in FIG. 10 includes emitters 1016 and detectors 1018 capable of being used for obtaining optical photoplethsymogram (PPG) measurements. Some PPG technologies rely on detecting light at a single spatial location, or adding signals taken from two or more spatial locations. Both of these approaches result in a single spatial measurement from which the heart rate (HR) estimate (or other physiological metrics) can be determined. In some embodiments, a PPG device employs a single light source coupled to a single detector (i.e., a single light path). Alternatively, a PPG device may employ multiple light sources coupled to a single detector or multiple detectors (i.e., two or more light paths). In other embodiments, a PPG device employs multiple detectors coupled to a single light source or multiple light sources (i.e., two or more light paths). In some cases, the light source(s) may be configured to emit one or more of green, red, and/or infrared light. For example, a PPG device may employ a single light source and two or more light detectors each configured to detect a specific wavelength or wavelength range. In some cases, each detector is configured to detect a different wavelength or wavelength range from one another. In other cases, two or more detectors configured to detect the same wavelength or wavelength range. In yet another case, one or more detectors configured to detect a specific wavelength or wavelength range different from one or more other detectors). In embodiments employing multiple light paths, the PPG device may determine an average of the signals resulting from the multiple light paths before determining an HR estimate or other physiological metrics. Such a PPG device may not be able to resolve individual light paths or separately utilize the individual signals resulting from the multiple light paths.

In some embodiments a user wearing the PPG device might perform an activity involving motion (or contorting of the wrist, for example, for a wrist-worn PPG device, thereby affecting the dynamics of the blood flow within the wrist). In such instances the accuracy of the HR estimate provided by the PPG device may be reduced or compromised. The light intensity received by the light detectors may be modulated by these movements typically at an order of magnitude or greater than the desired cardiac signal. Therefore, a preprocessing step where the signal effect of these movements is removed can be utilized to improve HR estimation accuracy during motion. In addition to the deleterious effects of motion, another cause of reduced signal quality in PPG devices may be the characteristics of the local area being sensed. For instance, signal quality can vary dramatically if a wrist-worn PPG sensor is moved only a few millimeters up or down the wrist. In addition, during motion, certain portions of the wrist-worn PPG devices may be subject to more motion depending on their location, position, and/or orientation, and PPG sensors placed on such portions may therefore result in greater degradation of the PPG signal due to motion.

Various embodiments enable a PPG device to utilize signals based on two or more independently addressable source-detector combinations such that the signal quality of the PPG device is improved, especially during activities involving motion. In some embodiments, PPG signals can be acquired via multiple light paths involving one or more sources and one or more detectors placed at different spatial locations. These multiple PPG signals can then be processed to isolate the cardiac component (e.g., by removing the motion component) from the PPG signals. For example, the motion component may be removed based on inputs from the accelerometer, unsupervised learning and/or previously done supervised learning. Additionally, or alternatively, the PPG signals corresponding to these multiple light paths are compared using a quality metric such that the highest-quality PPG signal can be selected to be used for estimating HR or other physiological metrics, as well as sleep time of or other potential aspects.

In order to utilize two or more source-detector pairs for motion signal rejection, a PPG device in accordance with various embodiments can use a computer program to identify the motion component of a given signal and remove the motion component from the composite signal, leaving only the cardiac signal as a remainder. In some implementations, the temporal phase of the cardiac waveform is assumed to stay constant between different light paths, while the phase of the motion signal is expected to vary between light paths due to how the PPG sensor interacts with the skin surface during activities involving motion (e.g., pressure at the PPG/skin interface may vary depending on the spatial location of the light source and the light detector of the light path). Using this concept, PPG devices can fit mathematical models to the spatial light path signals to identify the cardiac and motion components. First, PPG signals are extracted by each source-detector combination. For example, two light sources and two light detectors would result in four source-detector combinations. A mathematical model can then be fit to the different spatial points, from which characteristic signals are extracted related to the cardiac and motion components of the PPG signals. PPG devices may also implement other techniques including, but not limited to, independent component analysis (ICA) and other forms of blind source separation.

Although some embodiments are described with reference to HR or cardiac components of PPG signals, the techniques described herein may be extended to other types of physiological metrics described herein, such as may relate to $SpO_2$, or other types of signals that can be extracted from the PPG signals to determine such physiological metrics. For example, in some embodiments, a method for determining an $SpO_2$ value comprises receiving a first set of one or more PPG signals from one or more PPG sensors, which may include analog signals or digital data sampled from analog components and stored in computer memory. The first set of PPG signals may correspond to red and/or infrared light previously emitted by one or more emitters after the emitted light has interacted with the user's skin, when the monitoring device is worn by the user. A first set of PPG signals may include a noise component. The method for determining the $SpO_2$ value may further comprise receiving a second set of one or more PPG signals from the one or more PPG sensors or detectors, which may include analog signals or digital data sampled from analog components and stored in computer memory. For example, the second set of PPG signals may be obtained from different ranges of wavelengths emitted from the light source than the first set of PPG signals. For example, the second set of PPG signals may be obtained from one or more green light sources. In some cases, the second set of PPG signals is obtained from a system within the device used for tracking a user's heart rate. In other cases, the second set of PPG signals is received from a system separate from HR detection. The method for determining the $SpO_2$ value may further comprise filtering the first set of PPG signals based on a feature of the second set of PPG signals to generate a filtered set of PPG signals. Various filtering techniques may be used to remove noise or other features from the first set of PPG signals based on a feature of the second set of PPG signals. As one example, HR may be the feature of the second set of PPG signals. In the case of HR, the device may create a filter based at least in part upon the detected frequency of the HR signal. Examples of filters include a low-pass filter, a high-pass filter, and a narrow band filter that excludes frequencies that are inconsistent with the frequency of the HR signal. The method for determining the $SpO_2$ value may further comprise using one range of wavelengths to better measure an underlying signal on which the wavelengths of the first set of PPG signals operates. Based on this underlying signal (or features derived therefrom), the device can improve the first set of PPG signals based on filtering noise from the first set of PPG signals. Further, the filtered set of PPG signals can be used to create and store a $SpO_2$ value. As an example, the filtered set of PPG signals may have a reduced or eliminated noise component and therefore may serve as a more accurate basis for creating and storing the $SpO_2$ value.

In some embodiments, an intermediate HR estimation can be performed based on PPG signals from two or more light paths. For each of the acquired PPG signals, the PPG device may determine an estimate of the HR in beats-per-minute (BPM) and compute a confidence metric associated with the PPG signal, which is indicative of the signal quality for the particular light path associated with the PPG signal. It may also be possible to compute a confidence metric without an intermediate HR estimation, for example by characterizing characteristics (e.g., statistics) of the PPG signal or filtered versions of the PPG signal. In some embodiments, each confidence metric corresponds to a single PPG signal. In other cases, each confidence metric corresponds to multiple PPG signals. For example, a confidence metric may be computed for each way of combining the PPG signals (e.g., signals A+B, signals A+C, signals B+C, signals A+B+C, etc.), as well as for various combinations of PPG signals (e.g., selecting at least two of signals A, B, and C). In other cases, one confidence metric corresponds to a single PPG signal and another confidence metric corresponds to a combination of multiple PPG signals. The PPG device can select an HR estimate from the multiple HR estimates corresponding to the multiple light paths (e.g., by selecting the HR estimate of the PPG signal having the highest confidence metric). Alternatively, the PPG device may assign different weight values to the multiple HR estimates based on the confidence metric values associated with the individual and/or multiple PPG signals and compute a final HR estimate based on the weight values. The confidence values and/or the weight values may be updated or optimized using unsupervised machine learning. The PPG device may implement hysteresis logic which prevents jumping between light paths in a short time window if the confidence metric values corresponding to the two light paths are within a threshold value. The PPG device may also implement logic configured to bias the selection of HR estimates based on user data, activity data, movement data, or other data accessible by the PPG device. The PPG device may apply a smoothing filter on the HR estimates, for example, to improve accuracy and provide a better user experience.

One advantage of such an approach lies in the fact that the spatial information associated with the light sources and/or light detectors can be used by different algorithms to improve HR or other physiological metric estimation accuracy of the PPG sensing device, especially when the user of the device is exercising or performing activities involving motion. Existing implementations typically rely on algorithms to improve the HR or other physiological metric estimation performance, but do not have the benefit of the extra sensor data generated based on multiple light paths.

A light path represents an approximate path of light from a given source to a given detector. Thus, for example, if there are multiple sources and multiple detectors, then a distinct light path exist between each of the multiple sources and each of the multiple detectors. Thus, consistent with the embodiments described herein, PPG signals associated with any of the aforementioned light paths may be selectively obtained and utilized for estimating HR and/or other physiological metrics. For example, the PPG signals corresponding to any of multiple paths may be compared using a quality/confidence metric such as a signal-to-noise ratio (SNR), and the PPG signal having the highest quality can be selected to be used for estimating the HR and/or other physiological metrics.

An example PPG device may further comprise one or more processors 1002 coupled to memory 1004, a display 1006, a bus, one or more input/output (I/O) elements 1010, and wireless networking components 1012, among other such options. A display and/or I/O devices may be omitted in certain embodiments. If included, a display 1006 may provide an interface for displaying data, such as HR, blood oxygen saturation ($SpO_2$) levels, and other metrics of the user. For example, the processor 1002 may compute values for the physiological metrics monitored by the PPG device based on one or more PPG signals generated by the light detectors 1018. In an embodiment, the PPG device is a wristband and the display is configured such that the display faces away from the outside of a user's wrist when the user wears the PPG device. In other embodiments, the display may be omitted and data detected by the PPG device may be transmitted using the wireless networking interface via near-field communication (NFC), Bluetooth, Wi-Fi, or other suitable wireless communication protocols over at least one network 1020 to a host computer 1022 for analysis, display, reporting, or other such use.

The memory 1004 may comprise RAM, ROM, FLASH memory, or other non-transitory digital data storage, and may include a control program comprising sequences of instructions which, when loaded from the memory and executed using the processor 1002, cause the processor 1002 to perform the functions that are described herein. The emitters 1016 and detectors 1018 may be coupled to a bus directly or indirectly using driver circuitry by which the processor 1002 may drive the light emitters 1016 and obtain signals from the light detectors 1018. The host computer 1022 communicate with the wireless networking components 1012 via one or more networks 1020, which may include one or more local area networks, wide area networks, and/or internetworks using any of terrestrial or satellite links. In some embodiments, the host computer 1022 executes control programs and/or application programs that are configured to perform some of the functions described herein.

In some embodiments, each emitter 1016 can be individually controlled, or each light detector 1018 can be individually read out when multiple detectors are used, and in such embodiments, PPG sensor data along several different light paths can be collected. The control program can utilize the collected data to provide a more accurate estimation or HR and/or other physiological metrics. In related aspects, the processor 1002 and other component(s) of the PPG device may be implemented as a System-on-Chip (SoC) that may include one or more central processing unit (CPU) cores that use one or more reduced instruction set computing (RISC) instruction sets, and/or other software and hardware to support the PPG device.

In various embodiments, the emitters (or light sources) comprise electronic semiconductor light sources, such as LEDs, or produce light using any of filaments, phosphors, or laser. In some implementations, each of the light sources emits light having the same center wavelength or within the same wavelength range. In other cases, at least one light source may emit light having a center wavelength that is different from another one of the light sources. The center wavelengths of the light emitted by the light sources may be in the range of 495 nm to 570 nm. For example, a particular green light source may emit light with a center wavelength of 528 nm. In other embodiments, one or more of the light sources may emit red light (e.g., 660 nm center wavelength) or IR light (e.g., 940 nm center wavelength). In some embodiments, one or more of the light sources may emit light with peak wavelengths typically in the range of 650 nm to 940 nm. For example, in various embodiments, a particular red light source may emit light with a peak wavelength of 660 nm, and one or more infrared light sources may emit light with peak wavelengths in the range of 750 nm to 1700 nm. By way of example and not limitation, a particular infrared light source may emit light with a peak wavelength of 730 nm, 760 nm, 850 nm, 870 nm, or 940 nm. In some cases, commercial light sources such as LEDs may provide output at about 20 nm intervals with a center wavelength tolerance of +/−10 nm from the manufacturer's specified wavelength and thus one possible range of useful peak wavelengths for the light sources is 650 nm to 950 nm. The green light sources may be configured to emit light with wavelengths in the range of 495 nm to 570 nm. For example, a particular green light source may emit light with a wavelength of 528 nm. The green light sources may be equally spaced from light detectors as the pairs of red and infrared light sources. For example, if the distance between light detectors and a center of a first red light source is 2 mm, the distance between light detectors and a green light source may also be 2 mm (e.g., equidistant). In some other cases, the distance between the light detectors and one or more light sources is not equidistant. Further, in some embodiments, one or more of the light sources may comprise a single LED package that emits multiple wavelengths, such as green, red and infrared wavelengths, at the same or substantially the same (e.g., less than 1 mm difference) location with respect to multiple detectors. Such LEDs may include multiple semiconductor elements co-located using a single die in a single package.

The spacing of the light sources may be measured from the side of the light source or the center of the light detector. For example, the light sources may be configured such that the center of each light source is at a first distance from the edge of the closest one of the light detectors. In some embodiments, the first distance may be 2 mm. In some implementations, each light source is located at a second distance from the closest one of the light sources, and each light detector is located at a third distance from the closest one of the light detectors. In some embodiments, the second and third distances are identical to the first distance. In other embodiments, each of the second and third distances is different from the first distance. The second distance may be identical to or different from the third distance. The particular magnitude of the spacing may depend on a number of factors and this disclosure does not limit the embodiments to any particular spacing. For example, spacing in a range of 1 mm (or less) to 30 mm would be workable in various embodiments.

In some embodiments, independent control of all light sources is provided. In other embodiments, several light sources are controlled together as a gang or bank. A benefit of independent control of each light source, or independent readout from each of multiple detectors (e.g., obtaining independent signals based on the same or different light wavelengths from each of multiple detectors), is that a multiple light path approach may be used to improve the estimation of HR and/or other physiological metrics, as discussed further herein.

Light detectors may comprise one or more sensors that are adapted to detect wavelengths of light emitted from the light sources. A particular light source combined with a particular detector may comprise a sensor such as a PPG sensor. A first PPG sensor and a second PPG sensor can share components, such as the same light sources and/or detectors, or have different components and thus the term "PPG sensor," in addition to having its ordinary meaning, may refer to any of such arrangements although actual embodiments may use multiple components in implementing a PPG sensor. The term "PPG device," in addition to having its ordinary meaning, may refer to a device including a PPG sensor. A light detector, in an embodiment, may comprise one or more detectors for detecting each different wavelength of light that is used by the light sources. For example, a first detector may be configured to detect light with a wavelength of 560 nm, a second detector may be configured to detect light with a wavelength of 940 nm, and a third detector may be configured to detect light with a wavelength of 528 nm. Examples include photodiodes fabricated from semiconductor materials and having optical filters that admit only light of a particular wavelength or range of wavelengths. The light detectors may comprise any of a photodiode, phototransistor, charge-coupled device (CCD), thermopile detector, microbolometer, or complementary metal-oxide-semiconductor (CMOS) sensor. The light detectors may comprise multiple detector elements, as further described herein. One or more of the detectors may comprise a bandpass filter circuit.

In other embodiments, a detector may comprise one or more detectors configured to detect multiple wavelengths of light. For example, a single detector may be configured to tune to different frequencies based on data received from an electrical digital microprocessor coupled to detectors. In another way, the single detector may include multiple active areas where each active area is sensitive to a given range of wavelengths. In an embodiment, a single detector is configured to detect light with wavelengths in the red and IR frequencies and a second detector is configured to detect light with wavelengths in the green frequencies. Further, each of the light sources may use any of one or more different wavelengths of light as previously described.

In an embodiment, light detectors can be mounted in a housing with one or more filters that are configured to filter out wavelengths of light other than wavelengths emitted by light sources. For example, a portion of the housing may be covered with a filter which removes ambient light other than light in wavelengths emitted by light sources. For example, signals from light sources may be received at the light detectors through an ambient light filter that filters out an ambient light source that generates an ambient light with a wavelength that is different from the wavelength that is detected by the detector. Although LEDs and photodiodes are used as examples of the light sources and the light detectors, respectively, the techniques described herein may be extended to other types of light sources. For example, edge emitting lasers, surface emitting lasers, LED-pumped phosphors that generate broadband light. The techniques described herein may be extended to other combinations of light sources and detectors. For example, the PPG device may include (i) single or multiple LEDs and a multi-element photodetector (e.g., a camera sensor), (ii) an LED array and single or multiple photodiodes, (iii) a broadband LED-pumped phosphor and detector array with wavelength selective filters on each detector, (iv) spatial light modulator (SLM) (e.g., a digital micromirror device [DMD] or a liquid crystal on silicon [LCoS] device) and single or multiple LEDs, other combinations thereof, or other configurations of light sources and detectors.

Certain flow diagrams are presented herein to illustrate various methods that may be performed by example embodiments. The flow diagrams illustrate example algorithms that may be programmed, using any suitable programming environment or language, to create machine code capable of execution by a CPU or microcontroller of the PPG device. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, OBJECTIVE-C, C++, JAVA, or other human-readable languages and then compiled, assembled, or otherwise transformed into machine code that can be loaded into ROM, EPROM, or other recordable memory of the activity monitoring apparatus that is coupled to the CPU or microcontroller and then then executed by the CPU or microcontroller.

In an embodiment, PPG signals obtained from multiple light paths may be processed to filter or reject signal components that are associated with motion of the user, using a computer program to identify the motion component of the signal and remove the identified motion component from the composite signal, leaving the cardiac component as a remainder or final signal.

In an embodiment, PPG signals might be collected in variety of activities during day or at night, such as may relate to periods of walking, exercise, or sleep. Other on-device sensors including an accelerometer, gyroscope, or altimeter may be used to categorize or detect the activity, or human posture as a basis to develop the appropriate filters. These filters or signal processing methods might be used for targeted reduction of variability in the PPG data with multiple light paths. As an example and not limitation, the accelerometer data can be used to develop signal processing methods to filter the PPG data and look into a certain posture, removing other body orientations. This can help reduce the noise in the PPG data and get a better assessment of the corresponding physiological variables for the corresponding light paths.

In various embodiments, approaches discussed herein may be performed by one or more of: firmware operating on a monitoring or tracker device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for HR, SpO$_2$, and/or other physiological metrics. Alternatively, the monitoring device may execute operations relating to generating the monitoring signals and removing the motion components to produce a final estimate value for HR, SpO$_2$, and/or other physiological metrics local to the monitoring device. In this case, the final estimate may be uploaded or otherwise communicated to a server such as host computer that performs other operations using the value.

An example monitoring or tracker device can collect one or more types of physiological and/or environmental data from one or more sensor(s) and/or external devices and communicate or relay such information to other devices (e.g., host computer or another server), thus permitting the collected data to be viewed, for example, using a web browser or network-based application. For example, while being worn by the user, a tracker device may perform biometric monitoring via calculating and storing the user's step count using one or more sensor(s). The tracker device may transmit data representative of the user's step count to an account on a web service (e.g., www.fitbit.com), computer, mobile phone, and/or health station where the data may be stored, processed, and/or visualized by the user. The tracker device may measure or calculate other physiological metric(s) in addition to, or in place of, the user's step count. Such physiological metric(s) may include, but are not limited to: energy expenditure, e.g., calorie burn; floors climbed and/or descended; HR; heartbeat waveform; HR variability; HR recovery; respiration, SPO$_2$, blood volume, blood glucose, skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

An example tracker or monitoring device may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, a tracker device (and/or the host computer and/or another server) may collect data from one or more sensors of the device, and may calculate metrics derived from such data. For example, a tracker device may calculate the user's stress or relaxation levels based on a combination of HR variability, skin conduction, noise pollution, and/or sleep quality. In another example, a tracker device may determine the efficacy of a medical intervention, for example, medication, based on a combination of data relating to medication intake, sleep, and/or activity. In yet another example, a tracker device may determine the efficacy of an allergy medication based on a combination of data relating to pollen levels, medication intake, sleep and/or activity. These examples are provided for illustration only and are not intended to be limiting or exhaustive.

An example monitoring device may include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. A monitoring system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A wearable monitoring device, comprising:
   an attachment mechanism;
   a base coupled to the attachment mechanism;
   a plurality of light sources coupled to the base, each of the plurality of light sources configured to emit light at one or more respective wavelengths within a range including at least a carboxyhemoglobin absorption spectrum and an oxyhemoglobin absorption spectrum;
   a plurality of photodetectors coupled to the base to detect at least a portion of the light at the one or more respective wavelengths that is passed through or reflected by a subject, wherein the light detected by the plurality of photodetectors has traveled varying distances from the plurality of light sources;
   at least one of an accelerometer, an air detector, a pulsometer, or an electro-dermal sensor generating at least one secondary signal;
   biometric circuitry embedded within the wearable monitoring device and coupled to the plurality of photodetectors to receive one or more respective signals from the plurality of photodetectors and process the one or more respective signals to determine an intensity of wavelengths present in the light detected by the plurality of photodetectors, determine a measure of carboxyhemoglobin associated with the subject based at least in part on the intensity of the wavelengths, and analyze the measure of carboxyhemoglobin in view of the at least one secondary signal; and
   a communications system coupled to the biometric circuitry and configured to determine content for a notification to provide to a remote device, based at least in part on the measure of carboxyhemoglobin and the at least one secondary signal, and provide the notification to the remote device.

2. The wearable monitoring device of claim 1, wherein the attachment mechanism comprises a ring to be worn around a digit of the subject, and the base is located on an inner surface of the ring.

3. The wearable monitoring device of claim 1, wherein the attachment mechanism comprises an adhesive surface for adhering to the subject.

4. The wearable monitoring device of claim 1, wherein the biometric circuitry coupled to the plurality of photodetectors is configured to determine a smoking behavior of the subject based at least in part on a level of carbon monoxide inhalation corresponding to the measure of carboxyhemoglobin.

5. The wearable monitoring device of claim 1, wherein the biometric circuitry coupled to the plurality of photodetectors is configured to determine a condition of an environment to which the subject has been exposed based at least in part on a level of carbon monoxide inhalation.

6. A computer-implemented method, comprising:
   directing emitted light from a plurality of light sources of a wearable device towards a subject, the light inclusive of a wavelength spectrum corresponding to a carboxyhemoglobin absorption spectrum, the light traveling to a first depth for a first measurement, and the light traveling to a second depth for a second measurement;
   detecting received light, for the first measurement and the second measurement, via the subject, at a plurality of photodetectors of the wearable device;
   determining an intensity of wavelengths corresponding to the carboxyhemoglobin absorption spectrum present in the received light;
   determining a measure of carboxyhemoglobin present in the blood of the subject based at least in part on the intensity of wavelengths;
   obtaining at least one secondary signal from at least one of an accelerometer, an air detector, a pulsometer, or an electro-dermal sensor embedded in the wearable device;
   analyzing the measure of carboxyhemoglobin in view of the at least one secondary signal;
   determining content for a notification to provide to a remote device, based at least in part on the measure of carboxyhemoglobin and the at least one secondary signal; and
   generating the notification.

7. The computer-implemented method of claim 6, further comprising:
   determining an intensity of wavelengths corresponding to an oxyhemoglobin absorption spectrum present in the received light;
   determining a measure of oxyhemoglobin present in the blood of the subject based at least in part on the intensity of wavelengths corresponding to the oxyhemoglobin absorption spectrum;
   determining a first ratio between at least the measure of carboxyhemoglobin and the measure of oxyhemoglobin in the subject; and
   determining a carbon monoxide inhalation condition based at least in part on the first ratio.

8. The computer-implemented method of claim 7, further comprising:
   determining an intensity of wavelengths corresponding to a deoxyhemoglobin absorption spectrum present in the received light;
   determining a measure of deoxyhemoglobin present in the blood of the subject based at least in part on the intensity of wavelengths corresponding to the deoxyhemoglobin absorption spectrum;
   determining a second ratio between at least the measure of carboxyhemoglobin, the measure of oxyhemoglobin, and the measure of deoxyhemoglobin in the subject; and
   determining the carbon monoxide inhalation condition based at least in part on the second ratio.

9. The computer-implemented method of claim 6, further comprising:
spectrally resolving the received light, wherein the light emitted from the plurality of light sources is a full spectrum light.

10. The computer-implemented method of claim 6, wherein the plurality of light sources have different wavelength bands.

11. The computer-implemented method of claim 6, wherein the received light detected at the plurality of photodetectors is based on reflection of the emitted light from the subject.

12. The computer-implemented method of claim 6, wherein the received light detected at the plurality of photodetectors is based on transmission of the emitted light through the subject.

13. The computer-implemented method of claim 6, further comprising:
detecting the light at the plurality of photodetectors continuously or intermittently over a period of time; and
determining measures of carboxyhemoglobin in the subject over the period of time.

14. The computer-implemented method of claim 13, further comprising:
averaging the measures of carboxyhemoglobin obtained over the period of time.

15. The computer-implemented method of claim 6, further comprising:
determining that the measure of carboxyhemoglobin surpasses a threshold; and
generating an alert.

16. A wearable monitoring device, comprising:
a plurality of light sources;
a plurality of photodetectors corresponding to the one or more light sources;
at least one processor; and memory including instructions that, when executed by the at least one processor, cause the wearable monitoring device to:
direct emitted light from the plurality of light sources of the wearable monitoring device towards a subject, the light inclusive of a wavelength spectrum corresponding to a carboxyhemoglobin absorption spectrum, the light traveling to a first depth for a first measurement, and the light traveling to a second depth for a second measurement;
detect received light, for the first measurement and the second measurement, via the subject, at the plurality of photodetectors of the wearable monitoring device;
determine an intensity of wavelengths corresponding to the carboxyhemoglobin absorption spectrum present in the received light;
determine a measure of carboxyhemoglobin present in the blood of the subject based at least in part on the intensity of wavelengths;
obtain at least one secondary signal from at least one of an accelerometer, an air detector, a pulsometer, or an electro-dermal sensor embedded in the wearable monitoring device;
analyze the measure of carboxyhemoglobin in view of the at least one secondary signal;
determine content for a notification to provide to a remote device, based at least in part on the measure of carboxyhemoglobin and the at least one secondary signal; and
generate the notification.

17. The wearable monitoring device of claim 16, wherein the plurality of light sources include at least two light emitting devices corresponding to different spectral wavelengths.

18. The wearable monitoring device of claim 16, wherein the plurality of photodetectors include at least two detectors corresponding to different spectral wavelengths.

19. The wearable monitoring device of claim 16, wherein the instructions when executed further cause the system to:
determine an intensity of wavelengths corresponding to an oxyhemoglobin absorption spectrum present in the received light;
determine a measure of oxyhemoglobin present in the blood of the subject based at least in part on the intensity of wavelengths corresponding to the oxyhemoglobin absorption spectrum;
determine a ratio between at least the measure of carboxyhemoglobin and the measure of oxyhemoglobin in the subject; and
determine a carbon monoxide inhalation condition based at least in part on the ratio.

* * * * *